US009545246B2

(12) United States Patent
Lavender

(10) Patent No.: US 9,545,246 B2
(45) Date of Patent: Jan. 17, 2017

(54) ADJUSTABLE STOP FOR ELONGATE MEDICAL DEVICE DEFLECTION MECHANISM

(71) Applicant: St. Jude Medical, Atrial Fibrillation Division, Inc., St. Paul, MN (US)

(72) Inventor: Mark Lavender, Maple Grove, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 727 days.

(21) Appl. No.: 13/743,768

(22) Filed: Jan. 17, 2013

(65) Prior Publication Data

US 2014/0200560 A1  Jul. 17, 2014

(51) Int. Cl.
*A61B 1/00* (2006.01)
*A61B 17/00* (2006.01)
*A61B 18/14* (2006.01)

(52) U.S. Cl.
CPC ..... *A61B 17/00234* (2013.01); *A61B 18/1492* (2013.01); *A61B 2017/00318* (2013.01); *A61B 2017/00323* (2013.01); *A61B 2090/035* (2016.02); *Y10T 29/49826* (2015.01)

(58) Field of Classification Search
CPC .............. A61M 25/0147; A61B 1/0057; A61B 2017/003
USPC .................................................. 606/1, 41–52
See application file for complete search history.

(56) References Cited

U.S. PATENT DOCUMENTS

| 5,358,478 | A | 10/1994 | Thompson et al. |
| 5,904,667 | A | 5/1999 | Falwell |
| 6,171,277 | B1 | 1/2001 | Ponzi |
| 6,702,737 | B2 * | 3/2004 | Hino .................... A61B 1/0057 600/146 |
| 7,931,616 | B2 | 4/2011 | Selkee |
| 2011/0054446 | A1 | 3/2011 | Schultz |
| 2013/0324921 | A1 | 12/2013 | Reed |
| 2013/0324973 | A1 | 12/2013 | Reed |

FOREIGN PATENT DOCUMENTS

| JP | 2005218569 | 8/2005 |
| WO | 2008/055219 | 5/2008 |

* cited by examiner

*Primary Examiner* — Aaron Roane
(74) *Attorney, Agent, or Firm* — Dykema Gossett PLLC

(57) ABSTRACT

A deflection mechanism for an elongate medical device may comprise an actuator. The actuator may comprise a rotatable body comprising a channel, the channel comprising a plurality of recesses. The deflection mechanism may further comprises an activation wire having a proximal end and a distal end, and a wire lock attached to the proximal end of the activation wire. The wire lock may be disposed within the channel and configured to ride therein when the actuator body is rotated. An adjustable stop may be placed in one or more of the recesses of the channel so as to apply a force to the wire lock as the actuator is rotated so as to increase tension on the activation wire.

17 Claims, 12 Drawing Sheets

ADJUSTABLE STOP FOR ELONGATE MEDICAL DEVICE DEFLECTION MECHANISM

BACKGROUND a. Technical Field

This disclosure relates to elongate medical devices, such as, for example and without limitation, catheters and sheaths or introducers. More particularly, this disclosure relates to deflection mechanisms for such elongate medical devices, and elongate medical devices and components thereof that include such deflection mechanisms.

b. Background Art

It is known to use elongate medical devices, such as, for example, catheters and sheaths or introducers, when performing various therapeutic and/or diagnostic medical procedures on or in various anatomical structures of a patient's body, such as, for example, the heart. Such devices generally include an elongate shaft having a proximal end portion and a distal end portion, and a handle assembly disposed at the proximal end portion of the shaft. In order to precisely locate and position these devices within the anatomy of the patient, the devices may include means by which the device may be steered or guided as it travels within and through the patient's body. More particularly, these devices may include, among other components, deflection mechanisms that may be manipulated and controlled by a user or physician to allow for the precise locating and positioning of the device.

In general terms, such deflection mechanisms typically include, at least in part, an actuator and one or more activation wires. The actuator, which is generally associated with the handle assembly of the elongate medical device, is coupled to the activation wires and is configured to cause tension to be selectively applied thereto in order to deflect the shaft of the device in one or more directions. More particularly, each of the activation wires comprises a proximal end and a distal end. The proximal ends of the activation wires are coupled to the actuator, while the distal ends are coupled to one or more pull assemblies disposed at or near the distal end portion of the shaft of the device. As the actuator is manipulated, one or more of the activation wires may be selectively tensioned, thereby effecting movement of the pull assembly, and thus, the deflection of the shaft.

For example, in one conventional deflection mechanism, the actuator thereof comprises one or more posts that are each configured to be coupled to the proximal end of a respective activation wire. For example, in an instance wherein the deflection mechanism comprises a pair of activation wires, the actuator may include a pair of posts, each one of which has a respective one of the activation wires coupled thereto. In such an instance, as the actuator is manipulated to deflect the shaft in a desired direction, a pulling force is applied onto one of the activation wires, thereby causing tension to be applied to that activation wire, while a pushing force is applied to the other of the two activation wires.

The foregoing discussion is intended only to illustrate the present field and should not be taken as a disavowal of claim scope.

BRIEF SUMMARY

An embodiment of a deflection mechanism for use in an elongate medical device may comprise an actuator comprising a rotatable body, the body comprising a channel, the channel comprising a plurality of recesses, and an adjustable stop disposed in at least one of the recesses. The deflection mechanism may further comprise an activation wire having a proximal end and a distal end, and a wire lock attached to the proximal end of the activation wire. The wire lock may be disposed within the channel and may be configured to ride within the channel when the actuator body is rotated so as to increase tension on the activation wire.

An embodiment of a handle assembly for use in a steerable elongate medical device may comprise a housing defining a cavity and a deflection mechanism. The deflection mechanism may comprise an actuator comprising a rotatable body at least a portion of which is disposed within the cavity of the housing, the body comprising a channel. The deflection mechanism may further comprise an activation wire having a proximal end and a distal end, a wire lock attached to the proximal end of the activation wire, and an adjustable stop disposed across the channel so as apply a force to the wire lock responsive to actuation of said actuator. The channel may be configured to allow placement of the wire stop at multiple locations. The wire lock may be disposed within the channel and may be configured to ride therein when the actuator body is rotated. The activation wire may extend from the channel and into the cavity of the housing.

An embodiment of a method of manufacturing a handle assembly for an elongate medical device may comprise extending a proximal end of an activation wire into a channel of a rotatable body of the handle assembly and placing an adjustable stop in one or more of a plurality of recesses in the channel such that the activation wire extends through an opening in the adjustable stop and a wire lock at a proximal end of the activation wire cannot extend distally beyond the adjustable stop.

The foregoing and other aspects, features, details, utilities, and advantages of the present disclosure will be apparent from reading the following description and claims, and from reviewing the accompanying drawings.

DETAILED DESCRIPTION OF EMBODIMENTS

Various embodiments are described herein of various apparatus and/or systems. Numerous specific details are set forth to provide a thorough understanding of the overall structure, function, manufacture, and/or use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," "an exemplary embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," "in an exemplary embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
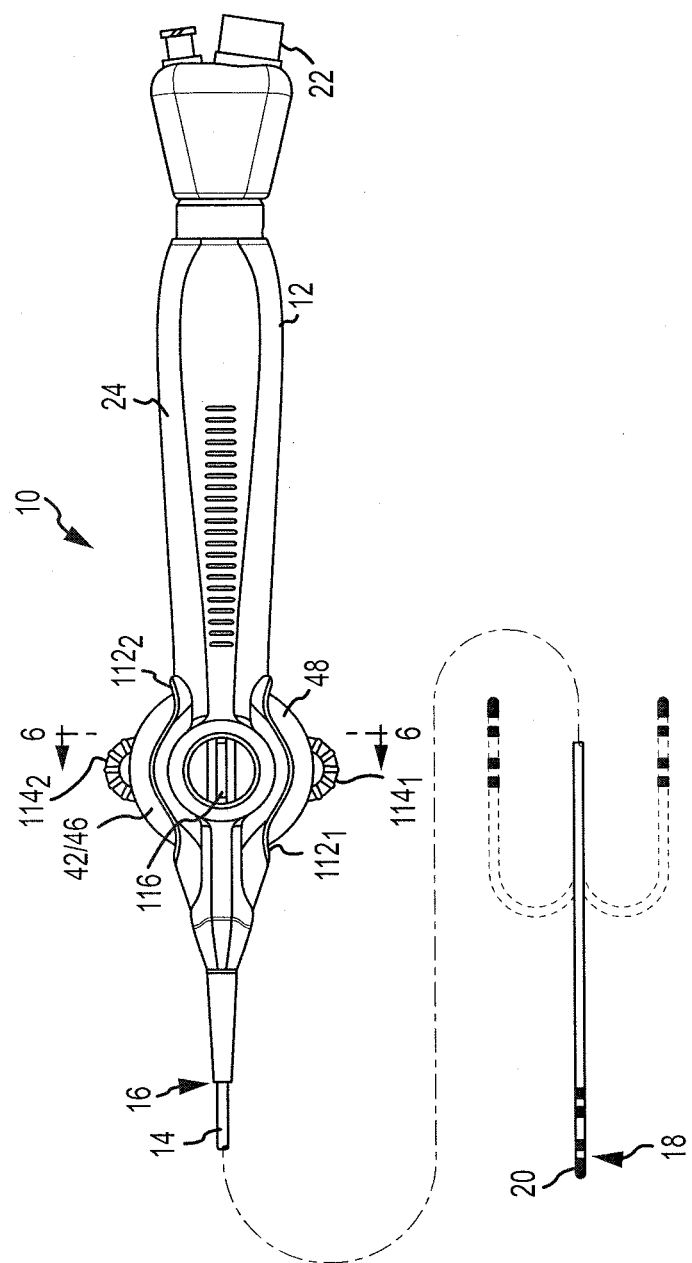
FIG. 1 is a plan view of an exemplary elongate medical device in accordance with the present teachings.

Referring now to the drawings wherein like reference numerals are used to identify identical or similar components in the various views, FIG. 1 illustrates one exemplary embodiment of an elongate medical device 10 that is configured to be deflected in one or more directions. The elongate medical device 10 may comprise, for example, a diagnostic and/or therapy delivery catheter, an introducer or sheath, or other like devices. For purposes of illustration and clarity, the description below will be with respect to an embodiment wherein the device 10 comprises a catheter (i.e., catheter 10). It will be appreciated, however, that embodiments wherein the device 10 comprises elongate medical devices other than a catheter remain within the spirit and scope of the present disclosure.

With continued reference to FIG. 1, in an exemplary embodiment, the catheter 10 is configured to be inserted into a patient's body, and more particularly, into the patient's heart. The catheter 10 may include a handle assembly or handle 12, a shaft 14 having a proximal end portion 16 and a distal end portion 18, and one or more sensors 20 mounted in or on the shaft 14. In an exemplary embodiment, the sensor(s) 20 is/are disposed at the distal end portion 18 of the shaft 14. The catheter 10 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

In an exemplary embodiment, the catheter 10 further comprises one or more electromechanical connectors 22 configured to allow the catheter 10, and the sensor(s) 20 thereof, in particular, to be coupled with components or subsystems of, for example, an electrophysiology (EP) laboratory system. Such components or subsystems may comprise, for example and without limitation, a visualization, navigation, and/or mapping system, an EP monitoring and recording system (e.g., for monitoring and/or recording electrocardiograms (EGM), cardiac signals, etc.), a tissue contact sensing system, an ablation system, a cardiac stimulation system (i.e., EP stimulator), and the like.

The handle 12 is disposed at the proximal end portion 16 of the shaft 14. The handle 12 provides a location for the clinician to hold the catheter 10 and, as will be described in greater detail below, may further provide means for steering or guiding the shaft 14 within the body of a patient.

Figure 2:
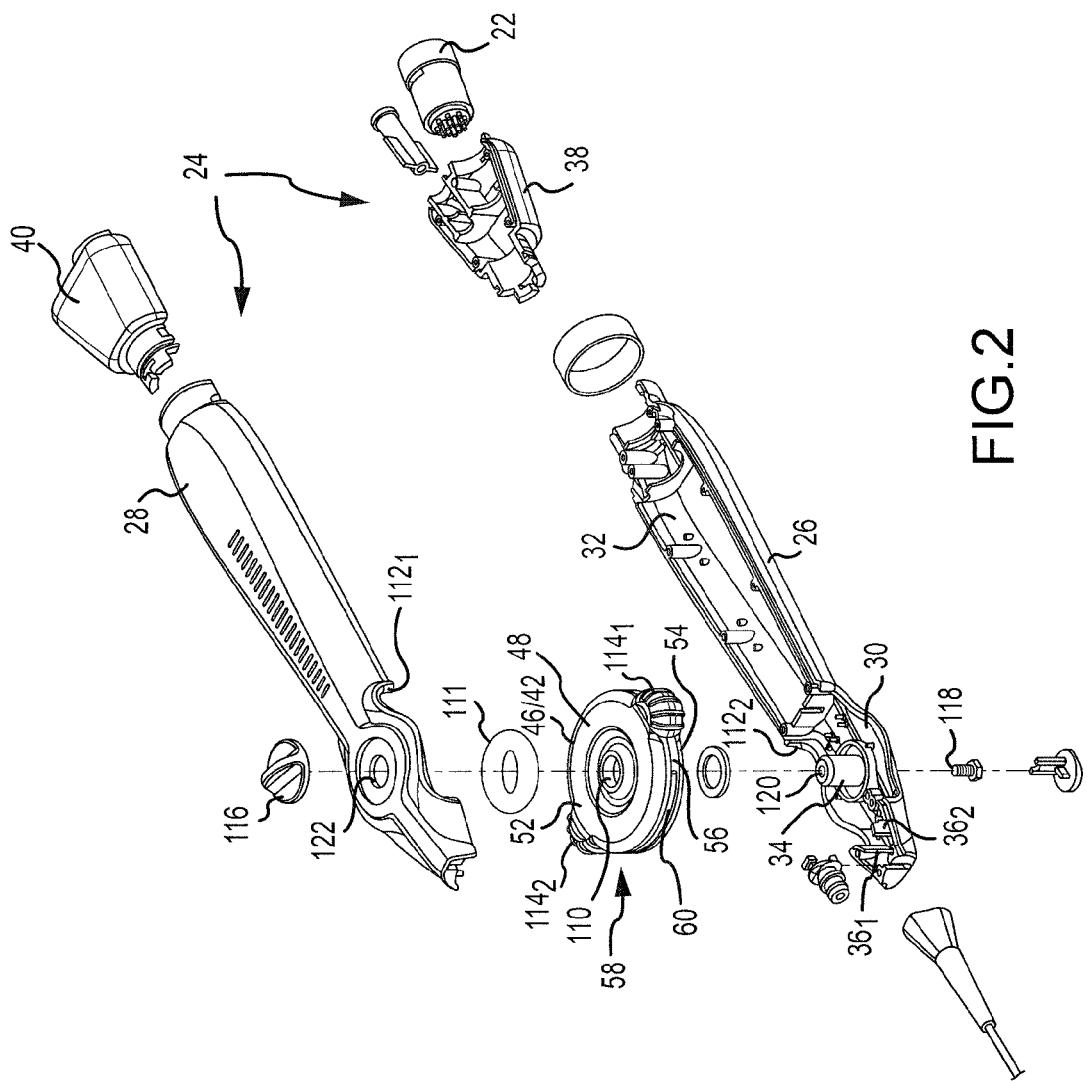
FIG. 2 is an exploded view of the exemplary elongate medical device illustrated in FIG. 1.

As illustrated in FIGS. 1 and 2, the handle 12 comprises a housing 24. The housing 24 may be of a unitary construction or may be constructed of a plurality of pieces that are configured to be assembled together. For example, and as illustrated in FIG. 2, the housing 24 may comprise a first or bottom piece 26 and a second or top piece 28. In such an embodiment, the first and second pieces 26, 28 of the housing 24 may be coupled together in any number of ways known in the art, such as, for example, by press fit or interference coupling techniques, by complementary interlocking members disposed on each piece 26, 28 of the housing 24, by conventional fasteners or adhesives, or any other techniques known in the art.

Figure 3A:
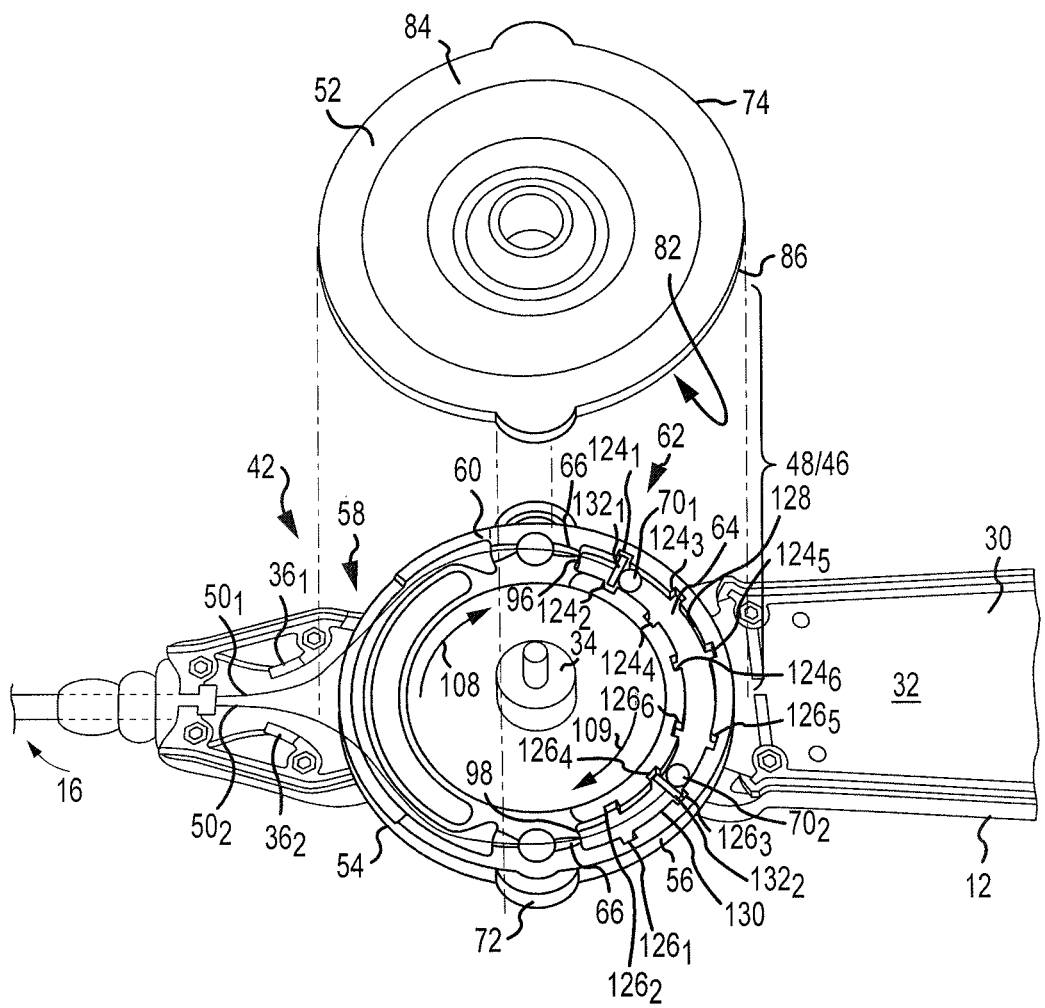
FIG. 3A is an isometric view of portions of the handle assembly and deflection mechanism of the elongate medical device illustrated in FIGS. 1 and 2 when the elongate medical device is in a neutral or non-deflected state.
Figure 3B:
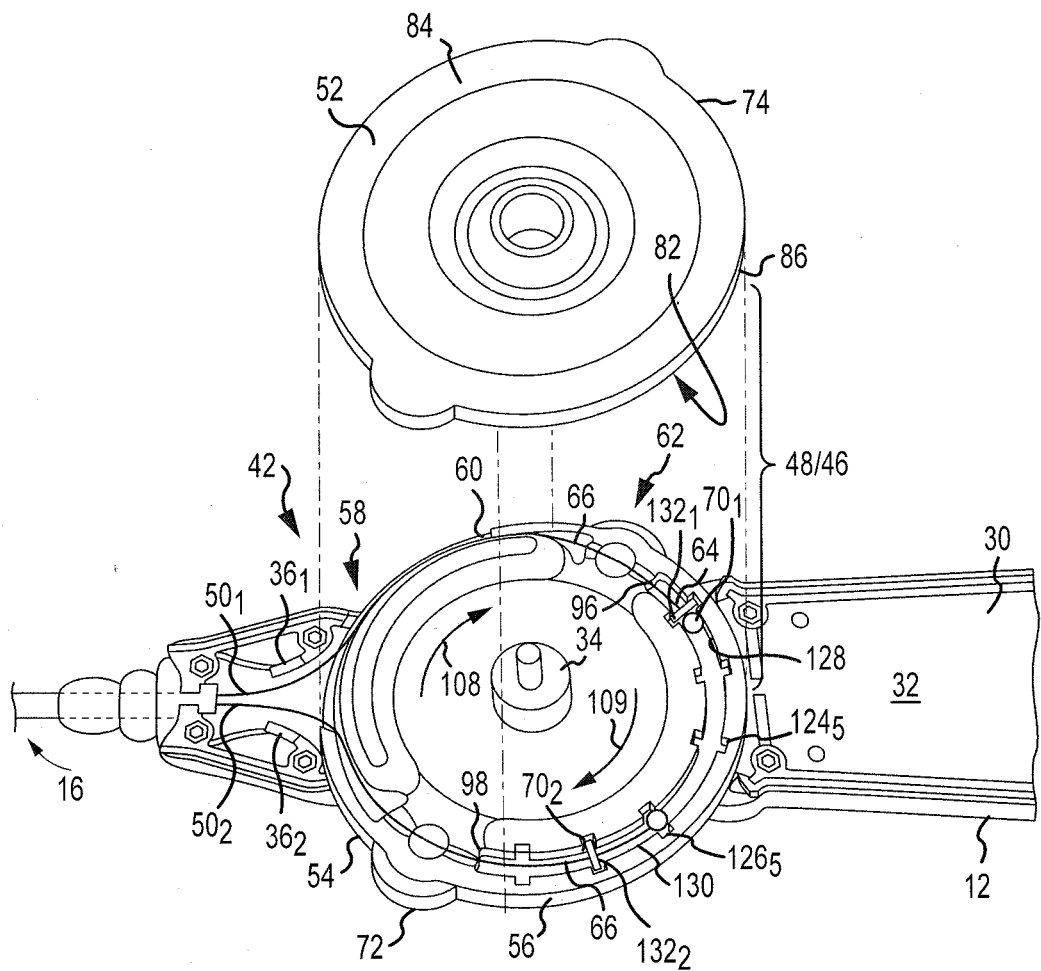
FIG. 3B is an isometric view of portions of the handle assembly and deflection mechanism of the elongate medical device illustrated in FIGS. 1 and 2 when the elongate medical device is in a deflected state.

Whether the housing 24 is formed of one or multiple pieces, the housing 24 comprises an inner surface 30 that defines a cavity 32 in the housing 24 that, as will be described below, is configured to house various components of the catheter 10 (e.g., the connector 22, various components of a deflection mechanism that will be described below, etc.). In an exemplary embodiment, and for purposes that will be described in greater detail below, the housing 24 further includes a post 34 protruding from the inner surface 30 and into the cavity 32. For purposes that will also be described more fully below, the housing 24 may further comprise a pair of guide walls $36_1$, $36_2$ extending or protruding from the inner surface 30 of the housing 24 and into the cavity 32. In such an embodiment, and as shown in FIGS. 3A and 3B, the guide walls $36_1$, $36_2$ are located between the proximal end portion 16 of the shaft 14 and the post 34. In any event, the handle 12 may be formed of conventional materials such as various types of plastics that are well known in the art.

The shaft 14 of the catheter 10 is an elongate, tubular, flexible member configured for movement within the body of the patient. The shaft 14 supports, for example and without limitation, sensors and/or electrodes mounted thereon, such as, for example, the sensor(s) 20, associated conductors, and possibly additional electronics used for signal processing and conditioning. The shaft 14 may also permit transport, delivery, and/or removal of fluids (including irrigation fluids, cryogenic ablation fluids, and bodily fluids), medicines, and/or surgical tools or instruments. An example of an irrigated shaft and associated catheter components is described in U.S. patent application Ser. No. 13/594,104, filed Aug. 24, 2012, incorporated herein by reference in its entirety as though fully set forth herein. The shaft 14 may be made from conventional materials such as polyurethane, and may define one or more lumens configured to house and/or transport electrical conductors, fluids, activation or steering wires, or surgical tools. In an embodiment wherein the catheter 10 is a diagnostic and/or therapeutic catheter, the shaft 14 may be introduced into a blood vessel or other structure within the body of a patient through a conventional introducer or sheath. As will be described in greater detail below, the shaft 14 may then be steered or guided through the body to a desired location, such as the heart.

The sensor(s) 20 mounted in or on the shaft 14 of the catheter 10 may be provided for a variety of diagnostic and therapeutic purposes including, for example and without limitation, electrophysiological studies, pacing, cardiac mapping, and ablation. In an exemplary embodiment, one or more of the sensors 20 are provided to perform a location or position sensing function. More particularly, and as will be described in greater detail below, one or more of the sensors 20 are configured to be a positioning sensor that provides information relating to the location (position and orientation, or "P&O") of the catheter 10, and the distal end portion 18 of the shaft 14 thereof, in particular, at certain points in time. Accordingly, in such an embodiment, as the catheter 10 is moved along a surface of a structure of interest of the heart and/or about the interior of the structure, the sensor(s) 20 can be used to collect location data points that correspond to the surface of, and/or other locations within, the structure of interest. These location data points can then be used for a number of purposes such as, for example and without limitation, the construction of surface models of the structure of interest.

With reference to FIGS. 1 and 2, the electromechanical connector 22 provides electrical and mechanical connection(s) for, among other things, the leads of the sensor(s) 20 of the catheter 10, as well as wires or cables extending between the catheter 10 and other components of, for example, an EP laboratory system. In an exemplary embodiment, and as illustrated in FIGS. 1 and 2, the connector 22 is disposed within the handle 12 of the catheter 10, and within the housing 24 thereof, in particular. For example, the connector 22 may be disposed within the cavity 32, and therefore, between the first and second pieces 26, 28 of the housing 24. Alternatively, and as illustrated in FIG. 2, the connector 22 may be disposed within a cavity defined by third and fourth pieces 38, 40 of the handle housing 24. In another exemplary embodiment, rather than being disposed within or as part of the handle 12, the connector 22 may be disposed apart from the handle 12, such as, for example, at the end of a pigtail (not shown) extending from the handle 12 of the catheter 10.

In addition to the components described above, in an exemplary embodiment, the catheter 10 further comprises a deflection mechanism 42 associated with the handle 12 of the catheter 10, and a pull assembly 44 (best shown in FIGS. 7A and 7B) disposed at or in the distal end portion 18 of the shaft 14 of the catheter 10. As will be described more fully below, the combination of the deflection mechanism 42 and the pull assembly 44 provides a means by which a user or physician can effect movement (e.g., deflection) of the distal end portion 18 of the shaft 14 in one or more directions, and therefore, allows the physician to steer the catheter 10.

With reference to FIGS. 2-3B, in an exemplary embodiment, the deflection mechanism 42 comprises, at least in part, an actuator 46 comprising a rotatable body 48 and one or more activation or steering wires 50. For purposes of clarity and illustration, the description below will be limited to an embodiment wherein the deflection mechanism 42 comprises first and second activation wires 50 (i.e., first activation wire $50_1$ and second activation wire $50_2$). It will be appreciated, however, that in other exemplary embodiments, the deflection mechanism 42 may comprise more or less than two activation wires, and therefore, such embodiments remain within the spirit and scope of the present disclosure.

In the embodiment illustrated in FIGS. 2-3B, and in general terms, the rotatable actuator body 48, which may be constructed of, for example, molded plastic, comprises a first outer wall 52, a second outer wall 54 that is substantially parallel to the first outer wall 52, and a third outer wall 56 that is transverse to and disposed between the first and second outer walls 52, 54. The actuator body 48 further comprises a first portion 58 having a slot 60 (best shown in FIG. 2) formed therein and a second portion 62 having a channel 64 disposed therein or thereon (best shown in FIGS. 3A and 3B). In an exemplary embodiment, and as will be described more fully below, the first portion 58 comprises a portion of the third outer wall 56 of the rotatable body 48 and the second portion 62 comprises an inner surface of one of the first and second outer walls 52, 54 of the rotatable body 48. Further, in an exemplary embodiment, the first and second portions 58, 62 of the body 48 are disposed at opposite ends of the body 48. As illustrated in FIGS. 3A and 3B, when the deflection mechanism 42 is assembled, the activation wires $50_1$, $50_2$ extend from the channel 64 and out of the rotatable body 48 through the slot 60.

Figure 7A:
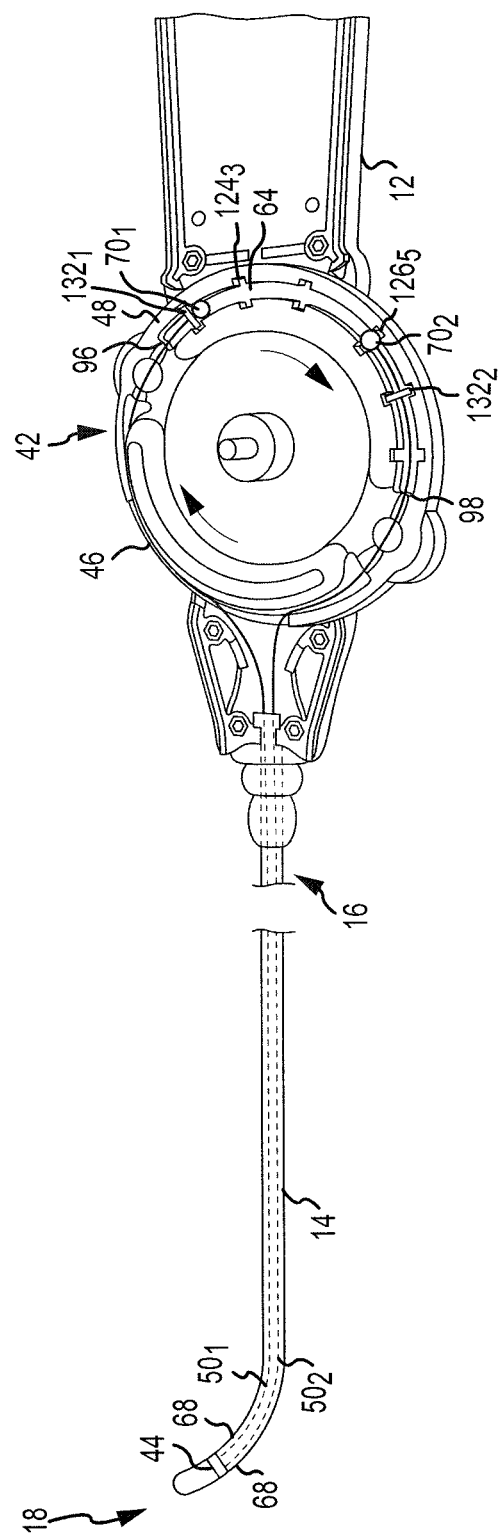
FIGS. 7A and 7B are isometric views of portions of the elongate medical device illustrated in FIG. 1 showing the distal end portion of the shaft of the elongate medical device deflected in different directions.
Figure 7B:
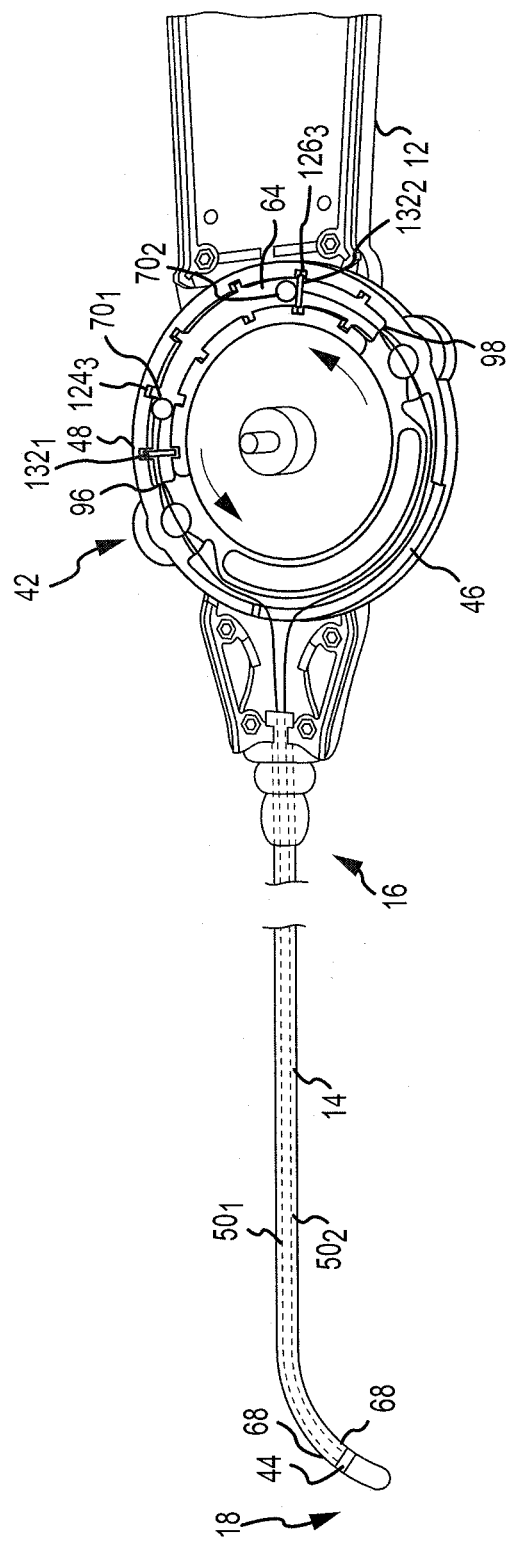

More particularly, each of the activation wires $50_1$, $50_2$ has a proximal end 66 and a distal end 68 (best shown in FIGS. 7A and 7B). In an exemplary embodiment, the deflection mechanism 42 further comprises a pair of anchors or wire locks 70. As illustrated, for example, in FIGS. 3A and 3B, each of the wire locks 70 is attached to the proximal end 66 of a respective activation wire 50 (i.e., a first wire lock $70_1$ is attached to the proximal end 66 of the first activation wire $50_1$, and a second wire lock $70_2$ is attached to the proximal end 66 of the second activation wire $50_2$). The wire locks 70 may be attached to the proximal ends 66 of the activation wires 50 in any number of ways. In one embodiment that is provided for exemplary purposes only and is not meant to be limiting in nature, each wire lock 70 is soldered onto the proximal end 66 of a respective activation wire 50. More particularly, in an embodiment such as that illustrated in FIGS. 8A and 8B, each wire lock 70 comprises a bore 71 therein within which the proximal end 66 of a corresponding activation wire 50 may be inserted and then soldered in place. It will be appreciated, however, that any number of attachment techniques that are well known in the art may be used instead of a soldering technique to attach the wire locks 70 to the proximal ends 66 of the activation wires 50, and such other techniques remain within the spirit and scope of the present disclosure. The wire locks 70 may alternatively be formed on or otherwise positioned along its respective activation wire 50 (e.g., at or near the proximal end 66 of its respective activation wire), such as, for example, by forming a knot in the respective activation wire 50. Other embodiments that do not utilize separate wire locks 70 may also be employed. For example, an activation wire may be secured to its respective adjustable stop (see, e.g., stops $132_1$, $132_2$ described in more detail below), such as by tying the activation wire around its respective adjustable stop.

As will be described in greater detail below, while the proximal ends 66 of the activation wires 50 are disposed within the actuator body 48 when the actuator 46 is assembled, the distal ends 68 of the activation wires $50_1$, $50_2$ are coupled or attached to, for example, the pull assembly 44 disposed within the shaft 14 of the catheter 10 (best shown in FIGS. 7A and 7B).

With continued reference to FIGS. 3A and 3B, in an exemplary embodiment, the channel 64 of the actuator body 48 includes a plurality of recesses $124_1$, $124_2$, $124_3$, $124_4$, $124_5$, $124_6$, $126_1$, $126_2$, $126_3$, $126_4$, $126_5$, $126_6$ (which may be referred to collectively as recesses 124, 126). For visual clarity, not all recesses 124, 126 are labeled in all figures, though all those illustrated are labeled in FIG. 3A. In an embodiment, the recesses are arranged in opposed pairs. For example, a first portion 128 of the channel 64 may include a first pair of opposed recesses $124_1$, $124_2$, a second pair of opposed recesses $124_3$, $124_4$, and a third set of opposed recesses $124_5$, $124_6$. A second portion 130 of the channel 64 may similarly include a first pair of opposed recesses $126_1$, $126_2$, a second pair of opposed recesses $126_3$, $126_4$, and a third set of opposed recesses $126_5$, $126_6$. Of course, a different number of recesses 124, 126 may be provided in one or both of the first and second channel portions 128, 130, in an embodiment. The recesses 124, 126 may comprise, in an embodiment, rectangular or squared notches. In a respective set of opposed recesses in each of the first and second portions 128, 130 of the channel 64, adjustable stops $132_1$, $132_2$ may be disposed so as to span the channel 64 substantially perpendicular to the channel 64 (i.e., perpendicular to the direction of movement of the activation wires $50_1$, $50_2$ and the wire locks $70_1$, $70_2$ within the channel). Accordingly, opposed recesses (for example, first opposed recesses $124_1$, $124_2$, $126_3$, $126_4$) may be configured so that a first recess $124_1$, $126_3$ receives a first end 134 (see FIGS. 9A-11C) of an adjustable stop $132_1$, $132_2$, and an opposed recess $124_2$, $126_4$ receives a second end 136 (see FIGS. 9A-11C) of an adjustable stop $132_1$, $132_2$. While the recesses in the embodiment depicted in FIGS. 3A and 3B are shown in pairs on opposing sides of the channel 64, in another embodiment, the recesses may only be positioned on only one side of the channel 64, such that the adjustable stop(s) may each be received on only one end 134 or 136 by a recess 124, 126.

The adjustable stops $132_1$, $132_2$ may be provided to ease the manufacturing and assembly processes of the catheter 10, and more particularly of the handle 12. During known manufacturing processes, the activation wires $50_1$, $50_2$ generally must be cut to an exact length to ensure that a neutral (i.e., non-rotated) state of the deflection mechanism 42 results in a neutral (i.e., non-deflected) position of the shaft 14. In known construction and assembly methods, tolerances for the length of the activation wires $50_1$, $50_2$ are generally tight. If an activation wire $50_1$, $50_2$ is too short, it may not extend sufficiently far into the channel 64, such that the neutral position of the deflection mechanism 42 is incorrect. If an activation wire $50_1$, $50_2$ is too long, it may extend too far into the channel 64 such that the deflection mechanism 42 does not enable the full range of deflection needed for the shaft 14.

With the adjustable stops $132_1$, $132_2$, the length tolerance for the activation wires $50_1$, $50_2$ may be eased. The activation wires $50_1$, $50_2$ may be designed and intended to have a length such that each activation wire $50_1$, $50_2$ (i.e., the wire locks $70_1$, $70_2$ thereof) reaches, for example only, a second set of opposed recesses (i.e., recesses $124_3$, $124_4$ in the first channel portion 128 and recesses $126_3$, $126_4$ in the second channel portion 130). If the activation wire $50_1$, $50_2$ is cut to the intended length, the adjustable stops $132_1$, $132_2$ can be placed in recesses $124_3$, $124_4$, $126_3$, $126_4$. If each of the activation wires $50_1$, $50_2$ is too long, the appropriate adjustable stop $132_1$, $132_2$ may be placed in the third set of opposed recesses (i.e., recesses $124_5$, $124_6$ or $126_5$, $126_6$). If one of the activation wires $50_1$, $50_2$ is too short, the appropriate adjustable stop may be placed in the first set of opposed recesses (i.e., recesses $124_1$, $124_2$ or $126_1$, $126_2$) or removed from the channel 64 entirely.

It should be understood that the placement of each adjustable stop $132_1$, $132_2$ will be dictated by the length of each activation wire $50_1$, $50_2$. Accordingly, the adjustable stops $132_1$, $132_2$ may be placed in different positions in the channel 64 (i.e., a first stop $132_1$ may be placed in a first set of opposed recesses $124_1$, $124_2$, and a second stop $132_2$ placed in a second set of opposed recesses $126_3$, $126_4$) or, as noted above, one or both of the adjustable stops $132_1$, $132_2$ may be removed entirely.

It should further be understood that features in addition to or instead of recesses 124, 126 may be provided, in an embodiment, to allow placement of the adjustable stops $132_1$, $132_2$. Accordingly, in an embodiment, the channel 64 may comprise structures and/or features in addition to or instead of the recesses 124, 126. For example, in an embodiment, the channel 64 may comprise inwardly-projecting tabs configured to hold an adjustable stop 132 in place. Such inwardly-projecting tabs may narrow the diameter of the channel 64. The inwardly-projecting tabs may be rectangular, in an embodiment, or may include some other shape or configuration. In an embodiment, the tabs may configured to eliminate the need for adjustable stops 132—i.e., a sufficient number of tabs may be included in the channel that virtually any neutral position length of an activation wire 152 would result in a set of inwardly-projecting tabs just proximal of the wire lock 70. In such an embodiment, one or more tabs may directly prevent a wire lock 70 from translating proximally beyond the one or more tabs.

Figure 8A:
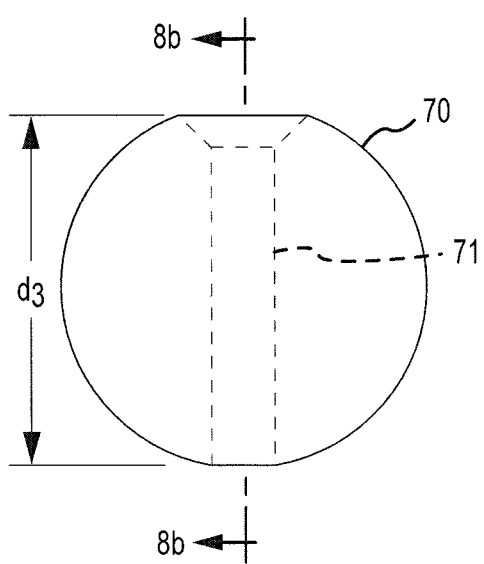
FIG. 8A is a side view of an exemplary embodiment of a wire lock of the deflection mechanism illustrated in FIGS. 1 and 2.
Figure 8B:
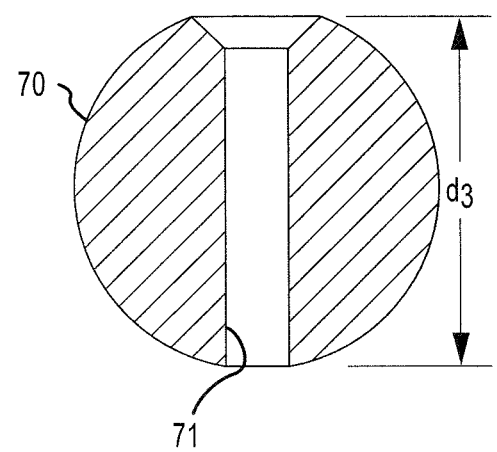
FIG. 8B is a cross-section view of the wire lock illustrated in FIG. 8A taken along the line 8B-8B in FIG. 8A.
Figure 9A:
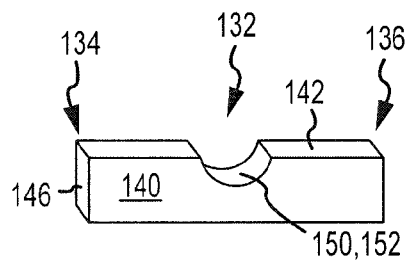
FIG. 9A is an isometric view of an embodiment of an adjustable stop.
Figure 9B:
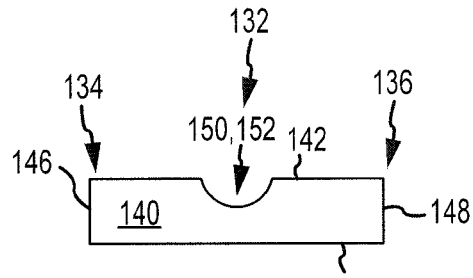
FIG. 9B is a side view of the adjustable stop of FIG. 9A.
Figure 9C:
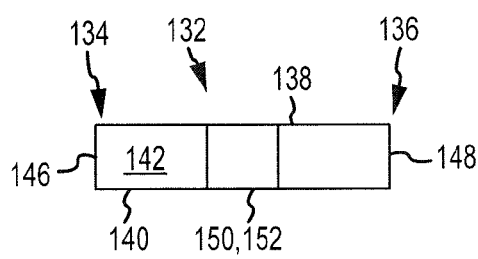
FIG. 9C is a bottom view of the adjustable stop of FIGS. 9A and 9B.
Figure 10A:
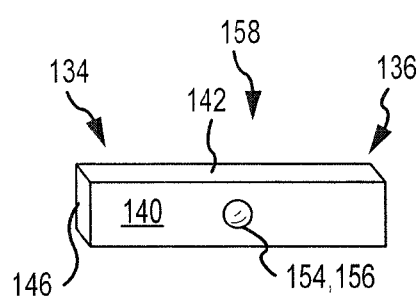
FIG. 10A is an isometric view of an embodiment of an adjustable stop.
Figure 10B:
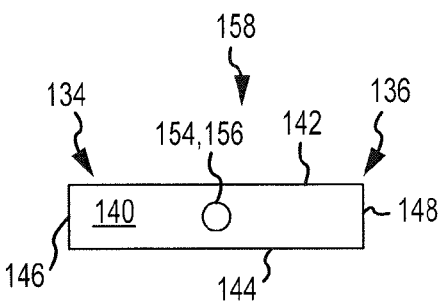
FIG. 10B is a side view of the adjustable stop of FIG. 10A.
Figure 10C:
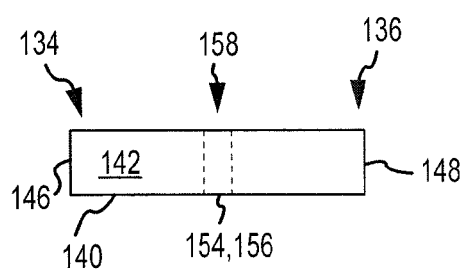
FIG. 10C is a top view of the adjustable stop of FIGS. 10A and 10B.
Figure 11A:
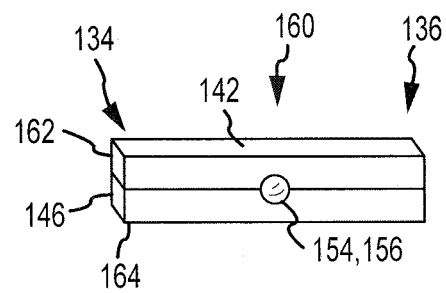
FIG. 11A is an isometric view of an embodiment of an adjustable stop.
Figure 11B:
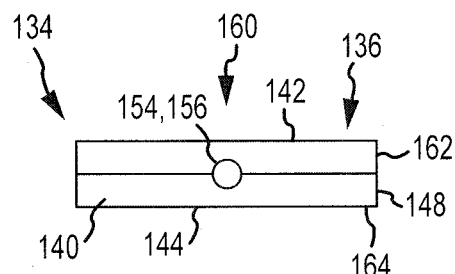
FIG. 11B is a side view of the adjustable stop of FIG. 11A.
Figure 11C:
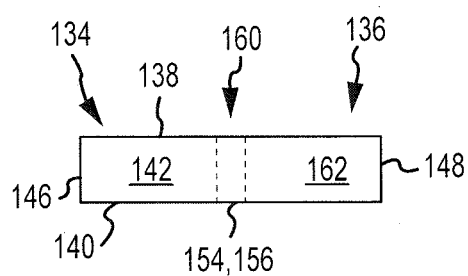
FIG. 11C is a top view of the adjustable stop of FIGS. 11A and 11B.

FIGS. 9A-9C illustrate a first embodiment of the adjustable stops $132_1$, $132_2$ (i.e., adjustable stop 132). FIG. 9A is an isometric view of the stop 132, FIG. 9B is a "bottom" view of the stop 132, and FIG. 9C is a "side" view of the stop 132. The stop 132 may comprise a rectangular prism, in an embodiment, including the first end 134, the second end 136, a first, proximal face 138, a second, distal face 140, a third, upper face 142, a fourth, lower face 144, two end faces 146, 148, and an opening 150 extending from the proximal face 138 to the distal face 140. The relative dimensions of the faces 138, 140, 142, 144, 146, 148 may be tailored to a particular application (i.e., the particular dimensions of the channel 64 and recesses 124, 126), and thus the stop 132 is not limited to the relative dimensions illustrated. The first and second ends 134, 136 of the stop may be generally squared, i.e., the end faces 146, 148 may be generally perpendicular to the proximal face 138, the distal face 140, the upper face 142, and the lower face 144. The opening 150 may be configured in size and shape to allow an activation wire (i.e., one of the activation wires $50_1$, $50_2$ in FIGS. 3A and 3B) to translate through or otherwise relative to the stop 132. The opening 150 may thus be larger in diameter than the activation wires $50_1$, $50_2$. The opening 50 may be further configured in size and shape to prevent a wire lock $70_1$, $70_2$ from passing through or past the stop 132. Thus, the size or diameter of the opening 150 may be smaller than a size or a diameter $d_3$ of the wire locks $70_1$, $70_2$ (see FIGS. 8A and 8B). In an embodiment, during manufacturing, activation wires may be pulled taut within a channel (i.e., the channel 64, see FIGS. 3A-5B) and the stops $132_1$, $132_2$ may be placed "down" in one or more recesses 124, 126, distal of the wire locks at the proximal end of the activation wires, with a respective activation wire passing through a respective opening 150.

The opening 150 may take any number of forms. For example, the opening may comprise a v- or u-shaped recess 152, as shown in FIGS. 9A-9C. In another exemplary embodiment, however, an opening 154 may comprise a hole, bore, or another like aperture 156, as shown in first alternate stop 158 in FIGS. 10A-10C and second alternate stop 160 in FIGS. 11A-11C. Accordingly, those of ordinary skill in the art will appreciate that an opening 150, 154 may take any number of forms, each of which remains within the spirit and scope of the present disclosure.

Referring to FIGS. 9A-9C and 10A-10C, the first alternate stop 158 may be substantially the same as the stop 132, except for the different openings 150, 154. Referring to FIGS. 9A-9C, 10A-10C, and 11A-11C, the second alternate stop 160 may also be substantially the same as the first alternate stop 158, except the second alternate stop 160 may comprise multiple pieces. For example, the second alternate stop 160 may comprise a first piece 162 and a second piece 164. The first piece 162 may include a first portion of the bore 156, the proximal face 138, the distal face 140, and the end faces 146, 148 and the second piece 164 may include a second portion of the bore 156, the proximal face 138, the distal face 140, and the end faces 146, 148. Of course, other constructions of the stops 132, 158, 160 are possible and contemplated.

Any of the stops 132, 158, 160 may be used as the stop $132_1$, $132_2$ in the deflection mechanism 42. Furthermore, the stops $132_1$, $132_2$ may be the same (e.g., both stops $132_1$, $132_2$ may comprise a stop 132), or the stops may be different from each other (e.g., one stop $132_1$ may comprise a stop 132, and another stop $132_2$ may comprise a first alternate stop 158).

Although the adjustable stops 132, 158, 160 are generally illustrated and described as rectangular prisms with generally flat faces 138, 140, 142, 144, 146, 148, other shapes of the adjustable stops 132, 158, 160 are possible and contemplated. In an embodiment, the shape and contours of an adjustable stop 132, 158, 160 may be designed according to the shape of the channel 64 and the shape and positions of the recesses 124, 126 in the channel 64 (see FIGS. 3A-5B).

Returning to FIG. 3, in an exemplary embodiment, the wire locks $70_1$, $70_2$ are disposed within the channel 64 of the actuator body 48 and are configured, in certain instances, to ride (e.g., slide or glide) therein as the actuator body 48 is rotated. Because the activation wires $50_1$, $50_2$ are attached to the wire locks $70_1$, $70_2$, and the wire locks $70_1$, $70_2$ are disposed within the channel 64, the activation wires $50_1$, $50_2$ extend from the channel 64 and out of the actuator body 48 through the slot 60 thereof.

Figure 4:
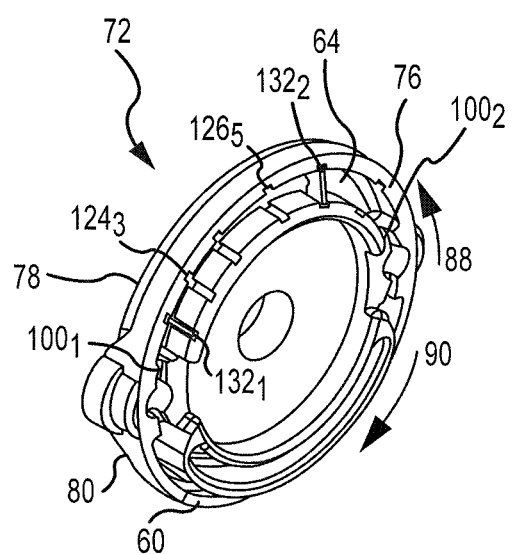
FIG. 4 is an isometric view of the base member of an exemplary actuator body of the deflection mechanism illustrated in FIGS. 1-3B.
Figure 5A:
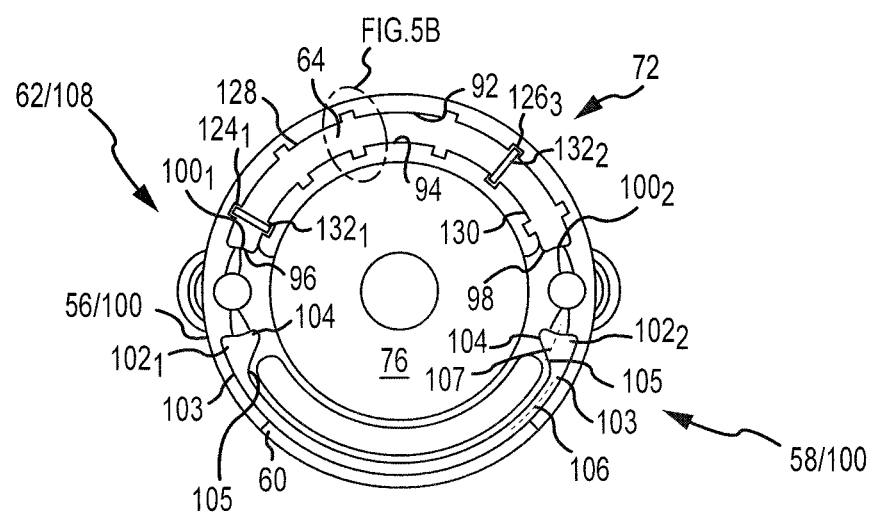
FIG. 5A is a plan view of a first face of the actuator body base member illustrated in FIG. 4.
Figure 5B:
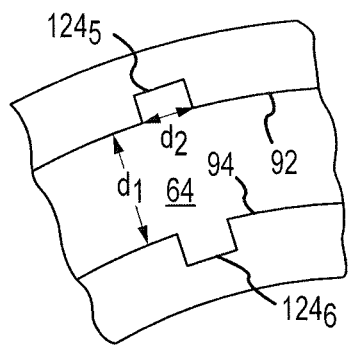
FIG. 5B is an enlarged plan view of a portion of the actuator body base member illustrated in FIG. 5A.
Figure 6:
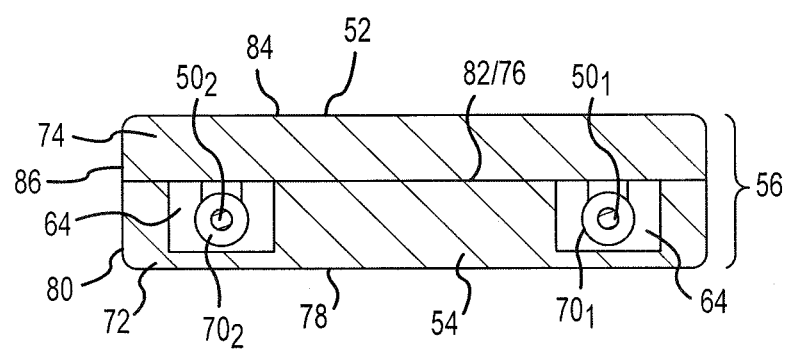
FIG. 6 is a cross-section view of an exemplary actuator of the deflection mechanism illustrated in FIGS. 1 and 2 taken along line 6-6 in FIG. 1.

More particularly, and with reference to FIGS. 3A-6, in one exemplary embodiment, the rotatable actuator body 48 comprises a base member 72 and a cover member 74. As best shown in FIGS. 4 and 6, the base member 72 comprises a first face 76, second face 78, and a transverse wall 80 disposed between and substantially perpendicular to the first and second faces 76, 78. In an exemplary embodiment, the transverse wall 80 of the base member 72 comprises the third outer wall 56 of the actuator body 48, and a portion of the transverse wall 80 further comprises the first portion 58 of the actuator body 48 having the slot 60 disposed therein. In such an embodiment, the first face 76 of the base member 72 may comprise the second portion 62 of the actuator body 48 that comprises the channel 64 disposed therein or thereon. As such, the first face 76 may comprise an inner surface of the first outer wall 52 of the actuator body 48, while the second face 78 may comprise an outer surface of the first outer wall 52.

Similar to the base member 72, in an exemplary embodiment such as that illustrated in FIGS. 3A, 3B, and 6, the cover member 74 of the actuator body 48 comprises a first face 82, a second face 84, and a transverse wall 86 disposed between and substantially perpendicular to the first and second faces 82, 84. The cover member 74 is adapted to overlie the base member 72, and the first face 82 of the cover member 74 is adapted to be engaged with the first face 76 of the base member 72. As such, in an exemplary embodiment, the first face 82 of the cover member 74 comprises an inner surface of the second outer wall 54 of the actuator body 48, while the second face 84 comprises an outer surface of the second outer wall 54. As will be described below, the cover member 74 is operative to retain at least the wire locks $70_1$, $70_2$ and the adjustable stops $132_1$, $132_2$ within the channel 64.

With reference to FIGS. 4 and 5A, the base member 72 of the actuator body 48 is illustrated. The base member 72 comprises a first end 88 and a second end 90 opposite the first end 88. In an exemplary embodiment, the channel 64 is disposed at the first end 88 of the base member 72, while the slot 60 is disposed at the second end 90. Further, in an exemplary embodiment, the channel 64 comprises a curved channel. In such an embodiment, and in an instance such as that illustrated in FIGS. 4 and 5A wherein the transverse surface 80 comprises an annular surface, the channel 64 may have a degree of curvature that is substantially the same as that of the transverse surface 80 of the base member 72.

In any event, and irrespective of whether the channel 64 is curved, the degree of curvature, or where it is located, in an exemplary embodiment the channel 64 comprises a substantially u- or v-shaped channel defined, at least in part, by first and second side walls 92, 94, and first and second end walls 96, 98. Each of the first and second end walls 96, 98 are disposed between the first and second end walls 92, 94 at opposite ends of the channel 64. The first and second side walls 92, 94 may have a plurality of recesses 124, 126, as discussed above.

In an exemplary embodiment, at least one of the end walls 96, 98 may have an opening 100 disposed therein. In the embodiment illustrated in FIGS. 4 and 5A, each of the end walls 96, 98 has an opening 100 disposed therein (i.e., the end wall 96 has an opening $100_1$ disposed therein, while the end wall 98 has an opening $100_2$ disposed therein). The openings $100_1$, $100_2$ are provided to allow for the extension of the activation wires $50_1$, $50_2$ out from the channel 64 within which the wire locks $70_1$, $70_2$, and therefore, the proximal ends 66 of the activation wires 50, are disposed. The openings $100_1$, $100_2$ may take any number of forms. For example, one or both of the openings $100_1$, $100_2$ may comprise a v- or u-shaped notch formed in the respective end walls 96, 98. In another exemplary embodiment, however, one or both of the openings $100_1$, $100_2$ may comprise a hole or another like aperture in the respective side walls 96, 98. Accordingly, those of ordinary skill in the art will appreciate that the openings $100_1$, $100_2$ may take any number of forms, each of which remains within the spirit and scope of the present disclosure. Regardless of the particular form of the openings $100_1$, $100_2$, the openings $100_1$, $100_2$ have a size (e.g., diameter) that is smaller than that of the wire locks $70_1$, $70_2$ so as to retain the wire locks $70_1$, $70_2$ within the channel 64, thereby preventing the wire locks $70_1$, $70_2$ from exiting the channel 64 through the openings $100_1$, $100_2$ if one or both of the adjustable stops $132_1$, $132_2$ are not present.

With continued reference to FIG. 5A, in addition to the channel 64, in an exemplary embodiment the second portion 62 of the actuator body 48, which in the illustrated embodiment comprises at least a portion of the first face 76 of the base member 72, further comprises one or more passageways 102 disposed therein or thereon extending from the slot 60 in the first portion 58 (e.g., the transverse surface 80 of the base member 72) to the opening(s) 100 in the channel 64. In an embodiment wherein the deflection mechanism 42 comprises a pair of activation wires $50_1$, $50_2$, first and second passageways $102_1$, $102_2$ are formed in or on the first face 76 of the base member 72. In such an embodiment, the first passageway $102_1$ extends from the slot 60 to the opening $100_1$ in the first end wall 96 of the channel 64, and the second passageway $102_2$ extends from the slot 60 to the opening $100_2$ in the second end wall 98. In an embodiment such as that illustrated in FIG. 5A, the first and second passageways $102_1$, $102_2$ comprise first and second portions of a larger passageway or groove disposed in or on the first face 76 of the base member 72. Alternatively, the first and second passageways $102_1$, $102_2$ may be separate and distinct from each other (i.e., do not comprise portions of a single larger groove or passageway).

As with the channel 64, in an exemplary embodiment, the passageways 102 may have a curved shape. In such an embodiment, and in an instance wherein the transverse surface 80 comprises an annular surface, the passageways 102 may have a degree of curvature that is substantially the same as the degree of curvature of the transverse surface 80 of the base member 72. Further, and as with the channel 64 and openings 100 described above, in an exemplary embodiment, the passageways $102_1$, $102_2$ may comprise substantially u- or v-shaped passageways.

In an exemplary embodiment, each of the passageways $102_1$, $102_2$ has a constant width along the length of the passageways $102_1$, $102_2$. Alternatively, and as best illustrated in FIG. 5, different portions of the passageways $102_1$, $102_2$ may have different widths. For example, in the illustrated embodiment, each of the passageways $102_1$, $102_2$ has a first portion 103 proximate the slot 60, and a second portion 104 that is in closer proximity to the openings $100_1$, $100_2$, respectively, than the first portion 103. In an exemplary embodiment, the first portion 103 has a width that is less than the width of the second portion 104. As such, each passageway $102_1$, $102_2$ has a shoulder 105 disposed therein at the transition between the first and second portions 103, 104. Further, in an exemplary embodiment such as that illustrated in FIG. 5A, the first portion 103 defines a longitudinal centerline 106 that is offset from a longitudinal centerline 107 defined by the second portion 104. As a result, and as illustrated in FIG. 5A, while in an exemplary embodiment the longitudinal centerlines of the openings $100_1$, $100_2$ are aligned with both the longitudinal centerline of the channel 64 and the respective longitudinal centerlines 107 of the second portions 104 of the passageways $102_1$, $102_2$, the respective centerlines 107 of the second portions 104 of the passageways $102_1$, $102_2$ are offset from the respective centerlines 106 of the first portions 103. More particularly, in an exemplary embodiment, the centerlines 106 of the first portions 103 are offset from the centerlines 107 of the second portions 104 in a direction toward the third outer wall 56/transverse wall 80. One purpose of employing passageways 102 having varying widths and being arranged as described above is to allow for a greater degree of deflection as compared to other known deflection mechanisms wherein the centerlines of the openings in the channel are aligned with the centerline of the channel 64 and the centerlines of the entire passageways 102 that has a constant width along its length.

In the illustrated embodiment, each of the passageways $102_1$, $102_2$ are configured to have a respective one of the activation wires $50_1$, $50_2$ extend therethrough. More particularly, and with reference to FIGS. 3A, 3B, and 5A, the first activation wire $50_1$ extends from the first wire lock $70_1$ disposed in the channel 64, through the opening in the adjustable stop $132_1$, through the opening $100_1$ in the end wall 96 of the channel 64, through the first passageway $102_1$, and out of the actuator body 48 through the slot 60 in the transverse surface 80 of the base member 72. Similarly, the second activation wire $50_2$ extends from the second wire lock $70_2$ also disposed in the channel 64, through the opening in the adjustable stop $132_2$, through the opening $100_2$ in the end wall 98 of the channel 64, through the second passageway $102_2$, and out through the slot 60.

As briefly described above, in an embodiment wherein the actuator body 48 is of a two-piece construction comprising the base member 72 and the cover member 74, the cover member 74 may be operative to engage the first face 76 of the base member 72 and to retain the wire locks $70_1$, $70_2$ and the adjustable stops $132_1$, $132_2$ in the channel 64. More particularly, FIG. 6 depicts a cross-sectional view of a portion of the actuator body 48 illustrating the cover member 74 overlying the base member 72, with the first face 82 of the cover member 74 being engaged with the first face 76 of the base member 72 to retain the wire locks $70_1$, $70_2$ in the channel 64.

Similarly, in an exemplary embodiment wherein the end walls 96, 98 of the channel 64 have respective openings $100_1$, $100_2$, therein, and/or the activation wires $50_1$, $50_2$ extend through the respective passageways $102_1$, $102_2$, the cover portion 74 is operative to retain the activation wires $50_1$, $50_2$ in the openings $100_1$, $100_2$, and/or the passageways $102_1$, $102_2$ in the same manner as that described above with respect to the wire locks 70. Finally, in an exemplary embodiment, the cover member 74 may be still further operative to retain the activation wires $50_1$, $50_2$ in the slot 60 of the actuator body 48 in the same manner as that described above.

Accordingly, once the wire locks 70, the adjustable stops 132$_1$, 132$_2$, and the activation wires 50$_1$, 50$_2$ are assembled with the base member 72, in an exemplary embodiment, the base member 72 and the cover member 74 may be coupled or affixed together using techniques that are well known in the art. For example, the base and cover members 72, 74 may be coupled together using press fit or interference coupling techniques, by complementary interlocking members disposed on each of the base and cover members 72, 74, by conventional fasteners or adhesives, or any other techniques known in the art. Alternatively, the base and cover members 72, 74 may not be coupled or affixed together at all, but rather may be held or compressed together by virtue of the particular construction of the handle 12 and the nature in which it is assembled (e.g., the when the handle 12 is fully assembled, the base and cover members 72, 74 are subjected to a compression force that is sufficient to hold the base and cover portions 72, 74 together as if they were otherwise coupled or affixed together).

Whether the second portion 58 of the actuator body 48, which, again, in the illustrated embodiment, comprises the base member 72 of the actuator body 48, includes only the channel 64 or both the channel 64 and the passageways 102$_1$, 102$_2$, each the end walls 96, 98 of the channel 64 are configured and operative to engage and apply a force onto a respective one of the wire locks 70$_1$, 70$_2$ when the actuator body 48 is rotated in a respective direction, if one or both of the adjustable stops 132$_1$, 132$_2$ are not included in the handle 24. Alternatively, if the adjustable stops 132$_1$, 132$_2$ are used, the stops 132$_1$, 132$_2$ are configured and operative to engage and apply a force onto a respective one of the wire locks 70$_1$, 70$_2$.

More particularly, and as illustrated in FIG. 3A, when the actuator body 48 is in a neutral position (i.e., the shaft 14 of the catheter 10 is in a neutral or non-deflected state), the wire locks 70$_1$, 70$_2$ disposed in the channel 64 are in contact with the adjustable stops 132$_1$, 132$_2$ or, if one or both of the adjustable stops 132$_1$, 132$_2$ are not used, one or both of the wire locks 70$_1$, 70$_2$ may be in contact with end walls 96, 98 of the channel 64, respectively. In an exemplary embodiment such as that illustrated in FIG. 3B, when the actuator body 48 is rotated in a first direction 108 (e.g., in a clockwise direction), the first adjustable stop 132$_1$ (or, if the first adjustable stop 132$_1$ is not used, the first end wall 96) of the channel 64 is operative to engage and apply a force onto the first wire lock 70$_1$. The force applied onto the first wire lock 70$_1$ by the stop 132$_1$ or the end wall 96 as the actuator body 48 is rotated clockwise causes tension to be applied to the first activation wire 50$_1$ (i.e., the first activation wire 50$_1$ is caused to be "pulled"). Conversely, as the actuator body 48 is rotated in the first direction 108, the second stop 132$_2$ and the second end wall 98 of the channel 64 move away from the second wire lock 70$_2$ and therefore, no force is applied onto the second wire lock 70$_2$. Rather, as illustrated in FIG. 3B, the second wire lock 70$_2$ rides within the channel 64 as the actuator body 48 rotates in the first direction 108, thereby preventing the second activation wire 50$_2$ from being either "pushed" or "pulled."

Similarly, the second stop 132$_2$ or the second end wall 98 of the channel 64 are operative to engage and apply a force onto the second wire lock 70$_2$ disposed in the channel 64 when the actuator body 48 is rotated in a second direction 109 opposite the first direction 108 (e.g., in a counterclockwise direction). As with the first activation wire 50$_1$ described above, the force applied onto the second wire lock 70$_2$ by the adjustable stop 132$_2$ or the end wall 98 as the actuator body 48 is rotated in the second direction 109 causes tension to be applied to the second activation wire 50$_2$ (i.e., the second activation wire 50$_2$ is caused to be "pulled"). Conversely, as the actuator body 48 is rotated in the second direction 109, the first stop 132$_1$ and the first end wall 96 of the channel 64 move away from the first wire lock 70$_1$, and therefore, no force is applied onto the first wire lock 70$_1$. Rather, the first wire lock 70$_1$ rides within the channel 64 as the actuator body 48 rotates in the second direction 109, thereby preventing the first activation wire 50$_1$ from being either "pushed" or "pulled."

In order to facilitate the riding of the wire locks 70 within the channel 64, in an exemplary embodiment such as that illustrated in FIGS. 8A and 8B, the wire locks 70 have a substantially spherical shape. It will be appreciated, however, that the present disclosure is not meant to be limited to such an embodiment, but rather in other exemplary embodiments that remain within the spirit and scope of the present disclosure, the wire locks 70 may have any number of shapes and such embodiments remain within the spirit and scope of the present disclosure.

Referring to FIGS. 5B, 8A, and 8B, the channel 64 may have a diameter $d_1$, one or more of the recesses may have an opening diameter $d_2$, and the wire locks 70 may have a diameter $d_3$. To facilitate the riding of the wire locks 70 within the channel 64, the diameter $d_3$ of the wire locks 70$_1$, 70$_2$ may be larger than the opening diameter $d_2$ and smaller than the diameter $d_1$ of the channel 64. In an embodiment, the ratio of the diameter $d_3$ of the wire locks to the recess opening diameter $d_2$ may be at least 4:1.

One advantage of the arrangement described above wherein the wire locks 70 are configured to ride within the channel 64 is that bending or buckling and weakening of the activation wires resulting from the pushing of the activation wires in a direction toward the catheter shaft 14 is prevented. More particularly, one drawback of certain conventional deflection mechanisms such as those described elsewhere herein has been with respect to pushing forces being applied to the activation wires that are not being selectively tensioned. More particularly, in certain conventional deflection mechanisms, the actuator thereof comprises one or more posts that are each configured to be coupled to the proximal end of a respective activation wire. For example, in an instance wherein the deflection mechanism comprises a pair of activation wires, the actuator may include a pair of posts, each one of which has a respective one of the activation wires coupled thereto. In such an instance, as the actuator is manipulated to deflect the shaft in a desired direction, a pulling force is applied onto one of the activation wires, thereby causing tension to be applied to that activation wire. Meanwhile, the other activation wire that is not subjected to the pulling force may be caused to be pushed in the opposite direction of the pulling force, and into, for example, the housing of the handle assembly. As a result of this pushing force, the activation wire being pushed may bend or buckle, thereby causing the activation wire to weaken and potentially fail (e.g., the activation wire may eventually snap).

In the present disclosure, because the wire locks 70 are configured to ride within the channel 64 as tension is applied to one of the activation wires 50 (i.e., the activation wire is "pulled" in the direction away from the catheter shaft 14), the wire lock 70 corresponding to the non-tensioned activation wire 50 is allowed to ride within the channel 64, and therefore, the non-tensioned activation wire 50 is not caused to be pushed, and thus, bending or buckling and weakening of that activation wire 50 resulting from the pushing of the activation wire 50 is prevented.

As briefly described above, and as illustrated in, for example, FIGS. 1, 3A, and 3B, the deflection mechanism 42 is associated with the handle 12 of the catheter 10. More particularly, in an exemplary embodiment, the actuator body 48 of the deflection mechanism 42 is rotatably mounted within a portion of the cavity 32 of the handle housing 24 and, in the illustrated embodiment, is disposed between the first and second pieces 26, 28 of the housing 24. As illustrated in FIG. 2, in an exemplary embodiment, the actuator body 48 has an aperture 110 extending therethrough configured to receive the post 34 of the handle housing 24. When the actuator body 48 is assembled with the post 34, the actuator body 48 is configured to rotate about the post 34.

In the illustrated embodiment wherein the catheter handle 12 comprises first and second pieces 26, 28, once the actuator body 48 is positioned within the cavity 32 and onto the post 34 of the housing 24, the housing 24 may be assembled together. More particularly, in an exemplary embodiment, the second piece 28 of the housing 24 may be aligned with the first piece 26 thereof and press fit together. As illustrated in FIG. 2, the handle 12 may further comprise an O-ring 111. The O-ring 111 may be disposed between the actuator body 48 and the first outer wall 52 thereof, in particular (which in one embodiment comprises the cover portion 74), and the inner surface of the housing 24 (which in one embodiment comprises the inner surface of the second piece 28 of the housing 24). As illustrated in FIGS. 1 and 2, in order to allow for a physician to manipulate or rotate the actuator body 48, the housing 24 of the handle 12 may further comprise one or more slots 112 therein through which the actuator body 48 extends and within which the actuator body 48 may rotate. In the embodiment illustrated in FIGS. 1 and 2, the housing 24 comprises a pair of slots $112_1$, $112_2$ disposed on diametrically opposite sides of the housing 24.

Further, in an embodiment such as that illustrated in, for example, FIGS. 1 and 2, while the actuator body 48 may rotate within the slot(s) 112 of the handle housing 24, it may comprise one or more protrusions 114 extending outwardly therefrom (e.g., from the third outer wall 56/transverse wall 80) that is/are configured to limit the extent to which the actuator body 48 may be rotated. More particularly, in the illustrated embodiment, which includes a pair of protrusions $114_1$, $114_2$ disposed on diametrically opposite sides of the actuator body 48, the protrusions $114_1$, $114_2$ extend outwardly a suitable distance such that when the protrusions $114_1$, $114_2$ reach an end of the respective slots $112_1$, $112_2$, they make contact with the housing 24, which thereby prevents the further rotation of the actuator body 48 in that particular direction.

In addition to limiting the rotation of the actuator body 48, the protrusions $114_1$, $114_2$ may further provide a means by which a physician using the catheter 10 can determine when the shaft 14 is in a neutral or non-deflected state. For example, when the protrusions $114_1$, $114_2$ are centered within the slots 112, the physician can tell that the shaft 14 is in a non-deflected state.

It will be appreciated that while the illustrated embodiment comprises a pair of protrusions 114, the present disclosure is not meant to be so limited. Rather, in other exemplary embodiments that remain within the spirit and scope of the present disclosure, the body 48 may comprise a single protrusion or more than two protrusions that serve the same function and purpose described above.

As briefly described above, the distal ends 68 of the activation wires $50_1$, $50_2$ of the deflection mechanism 42 are attached to the pull assembly 44 disposed within the shaft 14 of the catheter 10. The activation wires $50_1$, $50_2$ may be attached to the pull assembly 44 in an number of ways that are well known in the art, such as, for example and without limitation, by soldering or otherwise adhering the components together with a suitable adhesive. From the pull assembly 44, the activation wires $50_1$, $50_2$ extend through the shaft 14 to the proximal end portion 16 of the shaft 14. In an exemplary embodiment, the activation wires are disposed within one or more lumens (not shown) in the shaft 14. In any instance, and as illustrated in FIGS. 3A and 3B, the activation wires $50_1$, $50_2$ further extend from the proximal end portion 16 of the shaft 14 through the housing 24 of the handle 12, and the cavity 32 thereof, in particular, and into the slot 60 of the actuator body 48. As briefly described above, in an exemplary embodiment, the handle housing 24 may further comprise a pair of guide walls $36_1$, $36_2$ extending or protruding from the inner surface 30 of the housing 24 (and, in an exemplary embodiment, the first or bottom piece 26 thereof, in particular) and into the cavity 32. Each of the guide walls $36_1$, $36_2$ is configured to act as a guide for a respective one of the activation wires $50_1$, $50_2$ as the wires $50_1$, $50_2$ extend from the proximal end portion 16 of the shaft 14 and into the slot 60 of the actuator body 48.

In an exemplary embodiment, the handle 12 may further comprise means by which the ability to rotate the actuator body 48 may be controlled. For example, in the embodiment illustrated in FIG. 2, the handle 12 may include a tension knob 116 that is operative to increase or decrease the compression force applied to the actuator 46, and therefore, increase or decrease the ability to rotate the actuator body 48. One advantage of such functionality is that once a physician has deflected the shaft 14 a desired amount, the physician may maintain the deflection by adjusting the tension knob 116 to limit the ability to rotate the actuator body 48 in either direction.

In an exemplary embodiment such as that illustrated in, for example, FIG. 2, in addition to the tension knob 116, the handle 12 may further comprise a screw 118 that is configured to be mated with a threaded recess in the tension knob 116. In such an embodiment, the post 34 of the housing 24 may comprise a through-going bore 120, which may comprise a threaded bore, extending through the length of the post 34 and the outer surface of the housing 24 (e.g., through the outer surface of the first or bottom piece 26 of the housing 24). In such an embodiment, the housing 24 further comprises an aperture 122 that is coaxially aligned with the post 34, and the bore 120 thereof, in particular. In the illustrated embodiment, the aperture 122 is disposed in the second or top piece 28 of the housing 24. When the screw 118 and the tension knob 116 are assembled together, the shaft of the screw 118 extends through the bore 120, O-ring 111 (if applicable), and the aperture 122 in the housing 24. The tension knob 116 is mated with the end of the shaft of the screw 118, such as, for example, by threading the tension knob 116 onto the threaded shaft of the screw 118. Once assembled with the screw 118, the tension knob 116 can be adjusted to increase or decrease the compression force that is applied between the pieces 26, 28 of the housing 24, and the various components disposed therebetween. For example, the tightening of the tension knob 116 may result in an increase in the applied compression force, while the loosening of the tension knob 116 may result in a decrease in the compression force. The more compression force that is applied, the more the ability to rotate the actuator body 48 is limited.

As briefly described above, when assembled with the handle 12 and other components of the catheter 10, the deflection mechanism 42, and the actuator 46 thereof, in particular, is configured to be selectively manipulated to cause the distal end portion 18 of the shaft 14 to deflect in one or more directions. More particularly, the manipulation (e.g., rotation) of the body 48 of the actuator 46 causes the selective tensioning of the activation wires $50_1$, $50_2$, thereby effecting movement of the pull assembly 44 (e.g., a pull ring), and thus, the shaft 14.

For example, in the embodiment illustrated in FIGS. 7A and 7B, when the actuator body 48 is rotated in a clockwise direction, the activation wire $50_1$ is pulled in a direction that is away from the shaft 14 of the catheter 10, thereby applying tension to the activation wire $50_1$. The tensioning of the activation wire $50_1$ causes the pull assembly 44 to be pulled, resulting in the deflection of the shaft 14 in a first direction. Similarly, when the actuator body 48 is rotated in a counterclockwise direction, the activation wire $50_2$ is pulled in a direction that is away from the shaft 14 of the catheter 10, thereby applying tension to the activation wire $50_2$. The tensioning of the activation wire $50_2$ causes the pull assembly 44 to be pulled, resulting in the deflection of the shaft 14 in a second direction that is opposite the first direction.

Accordingly, the arrangement or configuration of the deflection mechanism 42 described herein above permits the manipulation of the actuator 46 thereof to allow a physician to steer and navigate the catheter 10 through the body of patient, while at the same time preventing the pushing of the activation wires 50 toward the shaft 14 of the catheter 10 and into a portion of the cavity 32 of the handle housing 24 that is forward of the actuator 46. As such, bending or buckling and weakening of the activation wires 50 resulting from such pushing of the activation wires 50 is prevented.

Although embodiments have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A deflection mechanism for use in an elongate medical device, comprising:
    an actuator comprising a rotatable body, said rotatable body comprising a channel, said channel comprising a plurality of recesses;
    an adjustable stop disposed in at least one of said recesses;
    an activation wire having a proximal end and a distal end; and
    a wire lock attached to said proximal end of said activation wire;
    wherein said wire lock is disposed within said channel and is configured to ride therein when said actuator body is rotated so as to increase tension on said activation wire when the actuator body is rotated in a first direction, and wherein said wire lock is further configured to move away from the adjustable stop when the actuator body is rotated in a second direction.

2. The deflection mechanism of claim 1, wherein said adjustable stop comprises an opening configured in size and shape to allow said activation wire to translate through said opening and to prevent said wire lock from passing said stop.

3. The deflection mechanism of claim 2, wherein said opening comprises a bore through said adjustable stop.

4. The deflection mechanism of claim 2, wherein said opening comprises a recess in a face of said stop.

5. The deflection mechanism of claim 1, wherein each of said recesses comprises an opening having a diameter that is smaller than a diameter of said wire lock.

6. The deflection mechanism of claim 5, wherein a ratio of said diameter of said wire lock to said opening is at least 4:1.

7. The deflection mechanism of claim 1, wherein said adjustable stop comprises a rectangular prism.

8. The deflection mechanism of claim 1, wherein said adjustable stop is a first adjustable stop, said activation wire is a first activation wire, and said wire lock is a first wire lock, the deflection mechanism further comprising:
    a second adjustable stop disposed in at least another of said recesses;
    a second activation wire having a proximal end and a distal end; and
    a second wire lock attached to said proximal end of said second activation wire;
    wherein said second wire lock is disposed within said channel and is configured to ride therein when said actuator body is rotated so as to increase tension on said second activation wire.

9. The deflection mechanism of claim 1, wherein said recesses are arranged in opposed pairs and said adjustable stop is disposed in two opposed recesses so as to span said channel generally perpendicular to a direction of translation of said activation wire.

10. The deflection mechanism of claim 1, wherein said channel is curved.

11. The deflection mechanism of claim 1, wherein said recesses are squared.

12. The deflection mechanism of claim 1, wherein said wire lock is spherical.

13. A handle assembly for use in a steerable elongate medical device, comprising:

a housing defining a cavity; and a deflection mechanism, said deflection mechanism comprising:

an actuator comprising a rotatable body at least a portion of which is disposed within said cavity of said housing, said rotatable body comprising a channel, said channel comprising a plurality of recesses;

an activation wire having a proximal end and a distal end;

a wire lock attached to said proximal end of said activation wire; and an adjustable stop disposed in at least one of said recesses so as to apply a force to said wire lock responsive to actuation of said actuator, wherein said channel is configured to allow placement of said adjustable stop at multiple locations;

wherein said wire lock is disposed within said channel and is configured to ride therein when said actuator body is rotated;

wherein said wire lock is further configured to increase tension on said activation wire when the actuator body is rotated in a first direction, and wherein said wire lock is further configured to move away from the adjustable stop when the actuator body is rotated in a second direction; and further wherein said activation wire extends from said channel and into said cavity of said housing.

14. The handle assembly of claim 13, wherein said adjustable stop comprises an opening, said activation wire extending through said opening, said opening configured in size and shape to prevent said wire lock from passing said adjustable stop.

15. The handle assembly of claim 13, wherein said channel comprises a plurality of recesses configured to receive said adjustable stop, each of said recesses comprising an opening having a diameter that is smaller than a diameter of said wire lock.

16. The handle assembly of claim 15, wherein said recesses are arranged in opposed pairs, wherein two recesses in an opposed pair are configured to receive opposite ends of said adjustable stop.

17. The handle assembly of claim 16, wherein said recesses are squared, and said ends of said adjustable stop are squared.

* * * * *